United States Patent
Levy et al.

(10) Patent No.: US 11,008,576 B2
(45) Date of Patent: May 18, 2021

(54) CHEMICALLY MODIFIED RNA APTAMERS AND USES THEREOF

(71) Applicant: ALBERT EINSTEIN COLLEGE OF MEDICINE, Bronx, NY (US)

(72) Inventors: Matthew Levy, Cary, NC (US); Arijit Bhowmick, Durham, NC (US)

(73) Assignee: ALBERT EINSTEIN COLLEGE OF MEDICINE, Bronx, NY (US)

( * ) Notice: Subject to any disclaimer, the term of this patent is extended or adjusted under 35 U.S.C. 154(b) by 43 days.

(21) Appl. No.: 16/336,532

(22) PCT Filed: Oct. 6, 2017

(86) PCT No.: PCT/US2017/055475
§ 371 (c)(1),
(2) Date: Mar. 26, 2019

(87) PCT Pub. No.: WO2018/075264
PCT Pub. Date: Apr. 26, 2018

(65) Prior Publication Data
US 2020/0181617 A1    Jun. 11, 2020

Related U.S. Application Data

(60) Provisional application No. 62/408,859, filed on Oct. 17, 2016.

(51) Int. Cl.
*C12N 15/115* (2010.01)
*C12N 15/10* (2006.01)

(52) U.S. Cl.
CPC .......... *C12N 15/115* (2013.01); *C12N 15/102* (2013.01); *C12N 2310/335* (2013.01)

(58) Field of Classification Search
None
See application file for complete search history.

(56) References Cited

U.S. PATENT DOCUMENTS

| | | |
|---|---|---|
| 9,382,533 B2 | 7/2016 | Zichi et al. |
| 2007/0117112 A1 | 5/2007 | Diener et al. |
| 2011/0269814 A1 | 11/2011 | Manoharan et al. |
| 2014/0363493 A1 | 12/2014 | Palliser et al. |
| 2015/0125516 A1 | 5/2015 | Levy et al. |
| 2015/0191730 A1 | 7/2015 | Levy et al. |
| 2016/0266133 A1 | 9/2016 | Levy |
| 2017/0304200 A1 | 10/2017 | Wilner et al. |

OTHER PUBLICATIONS

Fracknnan et al. Promega Notes No. 65, 1998, p. 27-30.*
PCT International Search Report and Written Opinion dated Feb. 23, 2018 in connection with PCT International No. PCT/US2017/055475, 9 pages.
Maier et al., "From selection hits to clinical leads: progress in aptamer discovery," Molecular Therapy—Methods & Development, Apr. 6, 2016, vol. 5, pp. 1-10.

* cited by examiner

*Primary Examiner* — Tracy Vivlemore
(74) *Attorney, Agent, or Firm* — Cantor Colburn LLP

(57) ABSTRACT

Provided are chemically modified ribonucleic acid (RNA) aptamers comprising one or more of 2'F guanylate, 2'OMe cytidylate, 2'OMe adenylate, and a deoxy pyrimidine nucleotide with a moiety on the 5 position of the pyrimidine; and methods of making the aptamers.

18 Claims, 12 Drawing Sheets
Specification includes a Sequence Listing.

```
                        SEQUENCE LISTING

<160> NUMBER OF SEQ ID NOS: 8

<210> SEQ ID NO 1
<211> LENGTH: 81
<212> TYPE: DNA
<213> ORGANISM: Artificial Sequence
<220> FEATURE:
<223> OTHER INFORMATION: Template used to test the effect of the
      position of the modified U on transcription

<400> SEQUENCE: 1
gggagtgtgt acgaggcatt acacgtagtg atcatgaatc gtgtgctaat acacggcggc      60
gaaccatgca tgcgggatag a                                                81

<210> SEQ ID NO 2
<211> LENGTH: 81
<212> TYPE: DNA
<213> ORGANISM: Artificial Sequence
<220> FEATURE:
<223> OTHER INFORMATION: Template used to test the effect of the
      position of the modified U on transcription

<400> SEQUENCE: 2
ggggaaggag agacgacgcg acacgtagtg atcatgaatc gtgtgctaat acacggcggc      60
gaaccatgca tgcgggatag a                                                81

<210> SEQ ID NO 3
<211> LENGTH: 88
<212> TYPE: DNA
<213> ORGANISM: Artificial Sequence
<220> FEATURE:
<223> OTHER INFORMATION: LRIG1 clone
```

```
<400> SEQUENCE: 3
gggaaggaga gacgacgcga cacccccttg agtcacaggt gtgtgagcgc cgacggcttg      60
gtacagcaga caagaccgga caagaagc                                        88

<210> SEQ ID NO 4
<211> LENGTH: 88
<212> TYPE: DNA
<213> ORGANISM: Artificial Sequence
<220> FEATURE:
<223> OTHER INFORMATION: LRIG1 clone

<400> SEQUENCE: 4
gggaaggaga gacgacgcga cacccgcttc accgctgtgt aactgcgacg acggacgtca      60
gatcagcaga caagaccgga caagaagc                                        88

<210> SEQ ID NO 5
<211> LENGTH: 59
<212> TYPE: DNA
<213> ORGANISM: Artificial Sequence
<220> FEATURE:
<223> OTHER INFORMATION: PD1 clone 2 truncation

<400> SEQUENCE: 5
gggaaggaga gacgacgcga cactcgaaaa tgctggagta acttcttaga gtacttggc       59

<210> SEQ ID NO 6
<211> LENGTH: 55
<212> TYPE: DNA
<213> ORGANISM: Artificial Sequence
<220> FEATURE:
<223> OTHER INFORMATION: PD1 clone 2 truncation

<400> SEQUENCE: 6
gggagagacg acgcgacact cgaaaatgct ggagtaactt cttagagtac ttggc           55

<210> SEQ ID NO 7
<211> LENGTH: 50
<212> TYPE: DNA
<213> ORGANISM: Artificial Sequence
<220> FEATURE:
<223> OTHER INFORMATION: PD1 clone 2 truncation

<400> SEQUENCE: 7
gggcgacgcg acactcgaaa atgctggagt aacttcttag agtacttggc                 50

<210> SEQ ID NO 8
<211> LENGTH: 47
<212> TYPE: DNA
<213> ORGANISM: Artificial Sequence
<220> FEATURE:
<223> OTHER INFORMATION: PD1 clone 2 truncation

<400> SEQUENCE: 8
cgacgcgaca ctcgaaaatg ctggagtaac ttcttagagt acttggc                    47
```

CHEMICALLY MODIFIED RNA APTAMERS AND USES THEREOF

CROSS-REFERENCE TO RELATED APPLICATIONS

This application is a U.S. national stage entry under 35 U.S.C. § 371 of PCT International Patent Application No. PCT/US2017/055475, filed Oct. 6, 2017, which claims the benefit of U.S. Provisional Patent Application No. 62/408,859, filed Oct. 17, 2016, the contents of each of which are incorporated herein by reference into the subject application.

STATEMENT OF GOVERNMENT SUPPORT

This invention was made with government support under grant number GM087985 awarded by the National Institutes of Health. The government has certain rights in the invention.

BACKGROUND OF THE INVENTION

Throughout this application various publications are referred to in parenthesis. Full citations for these references may be found at the end of the specification. The disclosures of all publications, patents and patent applications mentioned herein are hereby incorporated by reference in their entirety into the subject application to more fully describe the art to which the subject invention pertains.

Nucleotide aptamers are oligonucleotides that bind to a specific target molecule and have the potential to serve both diagnostic and therapeutic purposes. Nucleotide aptamers can be ribonucleic acid (RNA) or deoxyribonucleic acid (DNA) molecules, or comprise both ribonucleotide residues and deoxyribonucleotide residues, and are generally generated from large combinatorial libraries ($10^{14}$-$10^{15}$) of nucleic acids. This may be done by any method known in the art, such as by a process of in vitro selection or by SELEX (Systematic Evolution of Ligands by Exponential Enrichment) that targets a specific protein or molecular target. This is an iterative process consisting of essentially 1) an immunoprecipitation to partition away library molecules which bind a target and 2) amplification steps to regenerate the library. The cycle is typically repeated multiple times (typically 5-15) before functional molecules are identified. Aptamers are generated through a process that relies on binding. Aptamers are thus nucleic acids (oligonucleotides) that bind a specific protein or molecular target, typically with nanomolar or subnanomolar affinity. Generally, aptamers discriminate against molecules closely related to the target molecule.

To date, aptamers have been selected to bind hundreds of different targets ranging from small molecules to peptides to proteins (5-7). The approach has also been used to target whole cells and has even identified aptamers that can discriminate between different cell types without prior knowledge of specific ligands (8-10). Aptamers typically bind their targets with affinities in the nanomolar to picomolar range and can have specificities on par with the best monoclonal antibodies (11). One aptamer, Macugen®, which binds the vascular endothelial growth factor (VEGF), has been approved for the treatment of macular degeneration, and a number of other aptamers are in the pipeline or in various stages of development (1, 12).

As nucleic acids, aptamers possess some limitations that in recent years the field has strived to overcome. Most notably two major challenges faced by the field are 1) the in vivo stability of nucleic acids and 2) the lack of chemical diversity of nucleic acids.

The present invention combines advances in both these areas and provides a method that allows generation of highly stabilized, backbone modified RNA molecules that display enhanced chemical functionality.

SUMMARY OF THE INVENTION

The present invention provides methods for preparing a chemically modified ribonucleic acid (RNA) aptamer that binds to a target in a tissue or cell sample or surface or to a target protein or small molecule, the methods comprising: contacting a candidate mixture of RNAs with the tissue or cell sample, surface, protein or small molecule, wherein the mixture comprises 2'F guanylate, 2'OMe cytidylate, 2'OMe adenylate, and a deoxy pyrimidine nucleotide with a moiety on the 5 position of the pyrimidine, and wherein RNAs having affinity to the target bind the target and form RNA-target complexes; separating RNA-target complexes from free RNAs in the candidate mixture; and identifying chemically modified RNAs that bind to the target in the tissue or cell sample, surface, protein or small molecule, thereby preparing a chemically modified RNA aptamer that binds to a target in a tissue or cell sample or surface or to a target protein or small molecule.

The invention also provides chemically modified ribonucleic acid (RNA) aptamers comprising one or more of 2'F guanylate, 2'OMe cytidylate, 2'OMe adenylate, and a deoxy pyrimidine nucleotide with a moiety on the 5 position of the pyrimidine.

The present invention additionally provides pharmaceutical compositions comprising a therapeutically effective amount of any of the aptamers disclosed herein in a pharmaceutically acceptable carrier.

DETAILED DESCRIPTION OF THE INVENTION

Figure 1:
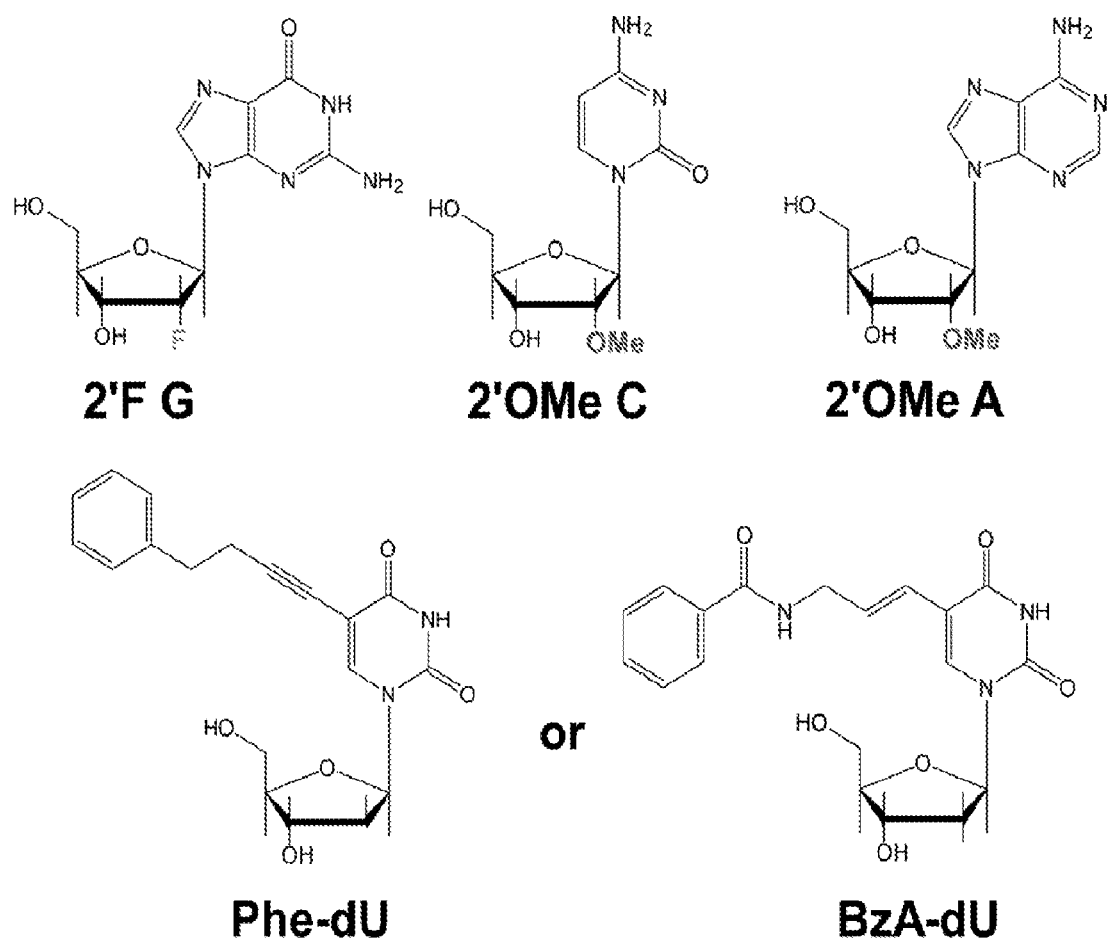
FIG. 1. Examples of nucleotide chemistry used for selection technology. Highly stable 2'F and 2'OMe backbone modification are combined with hydrophobically modified dU residues. Examples are nucleotides (triphosphates not shown).

The present invention provides a method for preparing a chemically modified ribonucleic acid (RNA) aptamer that binds to a target in a tissue or cell sample or surface or to a target protein or small molecule, the method comprising:

contacting a candidate mixture of RNAs with the tissue or cell sample, surface, protein or small molecule, wherein the mixture comprises 2'F guanylate, 2'OMe cytidylate, 2'OMe adenylate, and a deoxy pyrimidine nucleotide with a moiety on the 5 position of the pyrimidine, and wherein RNAs having affinity to the target bind the target and form RNA-target complexes;

separating RNA-target complexes from free RNAs in the candidate mixture; and identifying chemically modified RNAs that bind to the target in the tissue or cell sample, surface, protein or small molecule, thereby preparing a chemically modified RNA aptamer that binds to a target in a tissue or cell sample or surface or to a target protein or small molecule.

To find targeted binding nucleic acids, iterative rounds of selection can be performed. This involves a first round involving introducing a naïve library of nucleic acids and determining which bind the target. In successive rounds, only those nucleic acids that bound in the previous round are used. In this manner, only those nucleic acids that most strongly or most specifically bind and/or are integrated are selected.

Iterative rounds of selection maybe done by any method known in the art. This includes, but is not limited to, in vitro SELEX, whole-body SELEX, in vitro selection for internalization by cells, or whole-body selection for internalization by cells.

The candidate mixture of RNAs can be contacted, for example, with the tissue or cell sample, surface, protein or small molecule, and with a T7 RNA polymerase having one or more of the following mutations: Y639L, H784A and P266L. The T7 RNA polymerase can be, for example, a LAL-polymerase comprising the following mutations: Y639L, H784A and P266L. LAL is short hand used to refer to the Y639L, H784A, P266L T7 RNA polymerase mutant.

The mixture can comprise, for example, a buffer comprising 40 mM Tris [pH 8.3], 40 mM dithiothreitol (DTT), 1 mM spermidine, 0.01% Triton X-100, 50 mg/ml PEG-8000, 25 mM $MgCl_2$ and 10 mM $MnCl_2$. Preferably, the mixture comprises betaine. Betaine can be present, for example, at a final concentration of at least 1 M, preferably at a final concentration of 1-2.5 M.

Preferably, polynucleotides do not contain a thymine residue within the first 15 nucleotides of the polynucleotide. More preferably, polynucleotides do not contain a thymine residue within the first 20 nucleotides of the polynucleotide.

The 5'-modified deoxy pyrimidine nucleotide can be, for example, a modified deoxyuridine, 2'OMe, $2'NH_2$, 2'H or Locked nucleic acid (LNA) residue. The 5'-modified deoxy pyrimidine nucleotide can be, for example, Phe-dUTP, Bza-dUTP, isobutyl-dUTP, tyrosyl-dUTP, napthyl-dUTP, Phe-dCTP, Bza-dCTP, isobutyl-dCTP, tyrosyl-dCTP, or napthyl-dCTP. Phe-dUTP, Bza-dUTP, isobutyl-dUTP, tyrosyl-dUTP, napthyl-dUTP, Phe-dCTP, Bza-dCTP, isobutyl-dCTP, tyrosyl-dCTP, or napthyl-dCTP or another 5'-modified deoxy pyrimidine nucleotide can be present, for example, in a concentration of 1-2.5 mM. Preferably, Phe-dUTP, Bza-dUTP, isobutyl-dUTP, tyrosyl-dUTP, napthyl-dUTP, Phe-dCTP, Bza-dCTP, isobutyl-dCTP, tyrosyl-dCTP, or napthyl-dCTP or another 5'-modified deoxy pyrimidine nucleotide is present in a concentration of 2 mM.

Preferably, the moiety on the 5 position of the pyrimidine is a hydrophobic moiety.

Preferably, one or more of 2'F guanylate, 2'OMe cytidylate and 2'OMe adenylate is present in a concentration of 25 mM.

The invention also provides a chemically modified ribonucleic acid (RNA) aptamer comprising one or more of 2'F guanylate, 2'OMe cytidylate, 2'OMe adenylate, and a modified deoxy pyrimidine nucleotide with a moiety on the 5 position of the pyrimidine.

The 5'-modified deoxy pyrimidine nucleotide can be, for example, a modified deoxyuridine, 2'OMe, $2'NH_2$, 2'H or LNA residue. The 5'-modified deoxy pyrimidine nucleotide can be, for example, Phe-dUTP, Bza-dUTP, isobutyl-dUTP, tyrosyl-dUTP, napthyl-dUTP, Phe-dCTP, Bza-dCTP, isobutyl-dCTP, tyrosyl-dCTP, or napthyl-dCTP. Preferably, the moiety on the 5 position of the pyrimidine is a hydrophobic moiety.

The 5'-modified deoxy pyrimidine nucleotide can consist, for example, of a triphosphate of a structure selected from the following:

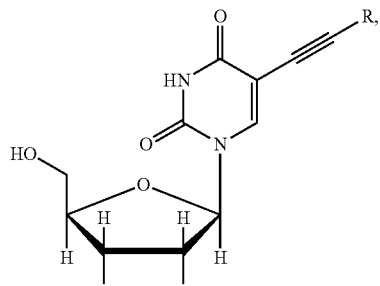

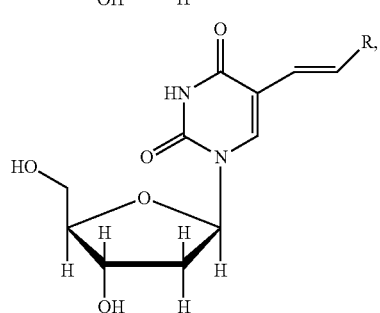

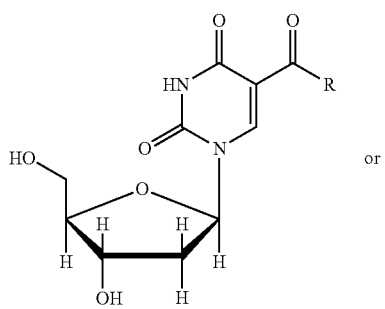

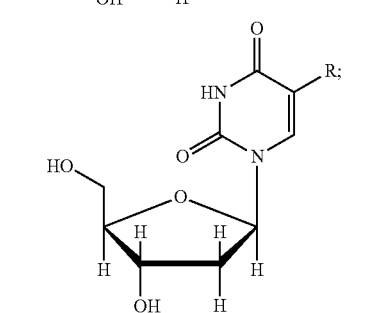

wherein R is

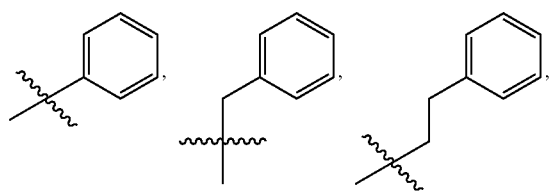

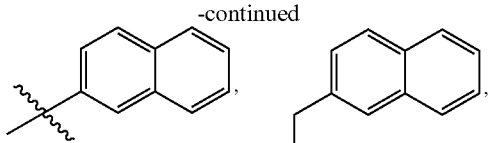

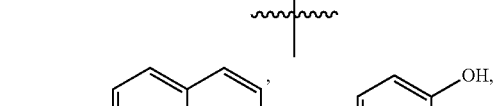

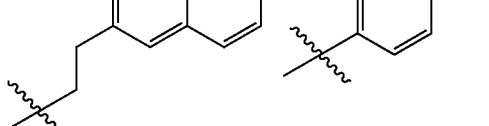

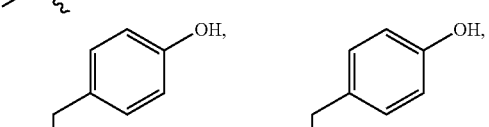

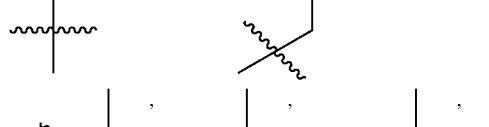

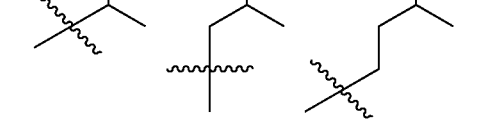

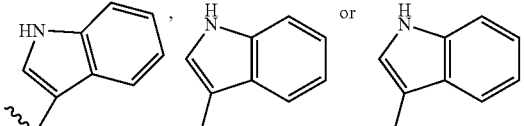

wherein ∼ represents the point of attachment of the R group to the pyrimidine or modified pyrimidine.

Other functional groups, e.g., larger, smaller, charged, etc., and other linker lengths, e.g. C4, C5, C6, C7 and C8, and other linkage positions on R-groups can also be used.

The aptamer can comprise one or more of nucleotide sequence (SEQ ID NO: 3)
GGGAAGGAGAGACGACGCGACACCCCCTTGAGTCACAGGTGTGTGAGCGC

CGACGGCTTGGTACAGCAGACAAGACCGGACAAGAAGC and (SEQ ID NO: 4)
GGGAAGGAGAGACGACGCGACACCCGCTTCACCGCTGTGTAACTGCGACG

ACGGACGTCAGATCAGCAGACAAGACCGGACAAGAAGC.

The aptamer can comprise one or more of nucleotide sequence (SEQ ID NO: 5)
GGGAAGGAGAGACGACGCGACACTCGAAAATGCTGGAGTAACTTCTTAGA

GTACTTGGC;

-continued (SEQ ID NO: 6)
GGGAGAGACGACGCGACACTCGAAAATGCTGGAGTAACTTCTTAGAGTAC
TTGGC;

(SEQ ID NO: 7)
GGGCGACGCGACACTCGAAAATGCTGGAGTAACTTCTTAGAGTACTTGGC;
and (SEQ ID NO: 8)
CGACGCGACACTCGAAAATGCTGGAGTAACTTCTTAGAGTACTTGGC.

In an embodiment of the methods or compositions, the aptamer is 20-175 nucleotides in length. In an embodiment, the aptamer is 25-150 nucleotides in length. In an embodiment, the aptamer is less than 60, less than 50, less than 40 or less than 30 nucleotides in length.

The aptamers of the invention may comprise nucleosides. A "nucleoside" as used herein is a glycosylamine consisting of a base bound to a ribose or deoxyribose sugar via a beta-glycosidic linkage. Examples include cytidine, uridine, adenosine, guanosine, thymidine and inosine. Nucleosides can be phosphorylated by specific kinases in the cell on the sugar's primary alcohol group (—CH$_2$—OH), producing nucleotides, which are the molecular building blocks of DNA and RNA. Nucleosides can be produced by de novo synthesis pathways, particularly in the liver, but they are more abundantly supplied via ingestion and digestion of nucleic acids in the diet, whereby nucleotidases break down nucleotides (such as the thymine nucleotide) into nucleosides (such as thymidine) and phosphate.

The aptamers of the invention may comprise nucleoside analogs. A "nucleoside analog" is a nucleoside structurally similar to the naturally occurring residues in RNA and DNA, used in medicine and in molecular biology, and which can be incorporated, e.g. chemically, into an oligonucleotide or nucleic acid by formation of a phosphodiester bond or equivalent with one or two residues of the residue chain depending on whether the nucleoside analog is in a terminal or intra-chain position, respectively. Nucleic acids are chains of nucleotides, which are composed of three parts: a phosphate backbone, a pucker-shaped pentose sugar, either ribose or deoxyribose, and one of five nucleobases. A nucleoside analogue differs from a nucleoside by having any one or more of its hydroxyl, base or sugar groups altered, as long as the alteration does not prevent the nucleoside analogue from being incorporated into an oligonucleotide such as an aptamer, internalizing nucleic acid or tumor-homing nucleic acid. In an embodiment of the invention the nucleoside analogue(s) are one or more of the following: a deoxyadenosine analog, a deoxycytidine analog, a deoxyguanosine analog, a (deoxy-)thymidine analog, and/or a deoxyuridine analog. Typically the analogue nucleobases confer, among other things, different base pairing and base stacking proprieties. The ribonucleic acid aptamers of the invention may thus comprise nucleoside analogs.

Nucleoside analogs as envisaged in the current invention include, but are not limited to, cytosine arabinoside, fludarabine, cladribine, acyclovir, 2',3'-dideoxyinosine; 9-β-D-ribofuranosyladenine; 1β-arabinofuranosylcytosine; arabinosylcytosine; 4-amino-5-fluoro-1-[(2R,5 S)-2-(hydroxymethyl)-1,3-oxathiolan-5-yl]-1,2-dihydropyrimidin-2-one; 2',3'-dideoxy-3'-thiacytidine; 2'-3'-dideoxycytidine; {(1 S,4R)-4-[2-amino-6-(cyclopropylamino)-9H-purin-9-yl]cyclopent-2-en-1-yl}methanol; 2-Amino-9-[(1S,3R,4S)-4-hydroxy-3-(hydroxymethyl)-2-methylidenecyclopentyl]-6,9-dihydro-3H-purin-6-one; 2'-3'-didehydro-2'-3'-dideoxythymidine; 1-(2-deoxy-β-L-erythro-pentofuranosyl)-5-methylpyrimidine-2,4(1H,3H)-dione; 1-[(2R,4 S,5 S)-4-azido-5-(hydroxymethyl)oxolan-2-yl]-5-methylpyrimidine-2,4-dione; 1-[(2R,4 S,5R)-4-hydroxy-5-(hydroxymethyl)oxolan-2-yl]-5-iodo-1,2,3,4-tetrahydropyrimidine-2,4-dione; 1-[4-hydroxy-5-(hydroxymethyl)oxolan-2-yl]-5-(trifluoromethyl)pyrimidine-2,4-dione; 5-Fluoro-2'-deoxycytidine; 5-Fluorodeoxycytidine; Floxuridine (5-Fluoro-1-[4-hydroxy-5-(hydroxymethyl)tetrahydrofuran-2-yl]-1H-pyrimidine-2,4-dione); 4-amino-1-(2-deoxy-2,2-difluoro-β-D-erythropentofuranosyl)pyrimidin-2(1H)-one; 2',2'-difluoro-2'-deoxycytidine; (8R)-3-(2-deoxy-β-D-erythropentofuranosyl)-3,4,7,8-tetrahydroimidazo [4,5-d][1,3] diazepin-8-ol.

Aptamers of the present invention can be administered by any appropriate route or means, including systemically, topically, parentally or enterally. In non-limiting examples, administration is by subcutaneous injection (aptamer bioavailability via subcutaneous administration is >80% in monkey studies (Tucker et al., *J. Chromatography* B. 732: 203-212, (1999)), intravenously, intranasally (lower and/or upper epithelia), or by direct injection into the desired body system, tissue or organ. With good solubility (>150 mg/mL) and comparatively low molecular weight (aptamer: 10-50 kDa; antibody: 150 kDa), a weekly dose of aptamer may be delivered by injection in a volume of less than 0.5 mL. In addition, the small size of aptamers allows them to penetrate into areas of conformational constrictions that do not allow for antibodies or antibody fragments to penetrate, presenting yet another advantage of aptamer-based therapeutics or prophylaxis.

T7 RNA polymerase with Y639L, H784A and P266L mutations is described in U.S. Pat. No. 8,105,813 B2, the contents of which is herein incorporated by reference.

As used herein "and/or", for example as in option A and/or option B, means the following embodiments: option A, option B, and the option A plus B.

The subject may be any subject. Preferably, the subject is a mammal. More preferably, the subject is a human.

The cells may be any cells from any tissue in the subject including but not limited to, blood, skeletal, breast, cardiac, neural, renal, pancreatic, gastric, liver, splenic, muscle, or pulmonary tissue. The cells may be normal, diseased, cancerous or may be infected with a virus or other pathogen.

The present invention additionally provides a pharmaceutical composition comprising a therapeutically effective amount of any of the aptamers provided herein. The pharmaceutically acceptable carrier must be compatible with the aptamer and not deleterious to the subject. Examples of acceptable pharmaceutical carriers include carboxymethylcellulose, crystalline cellulose, glycerin, gum arabic, lactose, magnesium stearate, methylcellulose, powders, saline, sodium alginate, sucrose, starch, talc, and water, among others. Formulations of the pharmaceutical composition may conveniently be presented in unit dosage and may be prepared by any method known in the pharmaceutical art. For example, the aptamer may be brought into association with a carrier or diluent, as a suspension or solution. Optionally, one or more accessory ingredients, such as buffers, flavoring agents, surface-active ingredients, and the like, may also be added. The choice of carriers can depend on the method of administration. In one embodiment, the aptamer is the sole active pharmaceutical ingredient in the formulation or composition. In another embodiment, there may be a number of active pharmaceutical ingredients in the formulation or composition aside from the aptamer.

All combinations of the various elements described herein are within the scope of the invention unless otherwise indicated herein or otherwise clearly contradicted by context.

Where a numerical range is provided herein, it is understood that all numerical subsets of that range, and all the individual integers contained therein, are provided as part of the invention. Thus, for example, an oligonucleotide which is from 5 to 25 nucleotides in length includes the subset of oligonucleotides which are 18 to 22 nucleotides in length, the subset of oligonucleotides which are 20 to 25 nucleotides in length etc. as well as a oligonucleotide which is 5 nucleotides in length, a oligonucleotide which is 6 nucleotides in length, a oligonucleotide which is 7 nucleotides in length, etc. up to and including a oligonucleotide which is 25 nucleotides in length.

This invention will be better understood from the Experimental Details, which follow. However, one skilled in the art will readily appreciate that the specific methods and results discussed are merely illustrative of the invention as described more fully in the claims that follow thereafter.

EXPERIMENTAL DETAILS

Introduction

SomaLogic, Inc. (Boulder, Colo.) has built a diagnostic platform using DNA aptamers with enhanced chemical functionality, which they call SOMAMER® (Slow Off-rate Modified Aptamers) (e.g., U.S. Pat. Nos. 7,947,447, 7,964,356, 8,975,026 and U.S. Patent Application Publication No. US2015/0148237). Their modifications of choice are hydrophobic groups appended to the 5-position of a deoxyuracil residue, which takes the place of dT during library generation. The inclusion of hydrophobic modifications in the DNA aptamer libraries has significantly improved the selection "hit rate". That is, when using regular DNA libraries, aptamers could only be generated to ~3 out of 10 proteins. However, with the new library technology, the hit rate improved to 8 or 9 out of 10 (2,3). Additionally, owing to their enhanced chemical functionality, these aptamers demonstrate improved binding characteristics (e.g., lower affinity, slower off-rates) when compared to traditional aptamers. However, it is important to note these aptamers are at root DNA molecules generated using a thermostable DNA polymerase (KOD DNA polymerase). As DNA they are not stable in biological solutions, and the backbone needs to be converted to more stabilizing residues. While stabilization via the incorporation of sugar backbone modifications is a tractable problem, it is non-trivial and requires the systematic chemical synthesis of dozens if not hundreds of variants to identify which 2' modifications are tolerable in functional molecules.

The Present Invention

The present invention provides a means to directly select and identify high affinity aptamers bearing hydrophobically modified (e.g., dU or dC) residues on a modified, nuclease stabilize RNA backbone composed of a mixture of 2'F and 2'OMe. More specifically, conditions have been developed to generate aptamer libraries composed of highly nuclease resistant 2'OMe ATP, 2'OMe CTP and 2'F GTP in combination with a deoxyuridine residue which bears a hydrophobic moiety on the 5 position (FIG. 1).

Figure 2A:
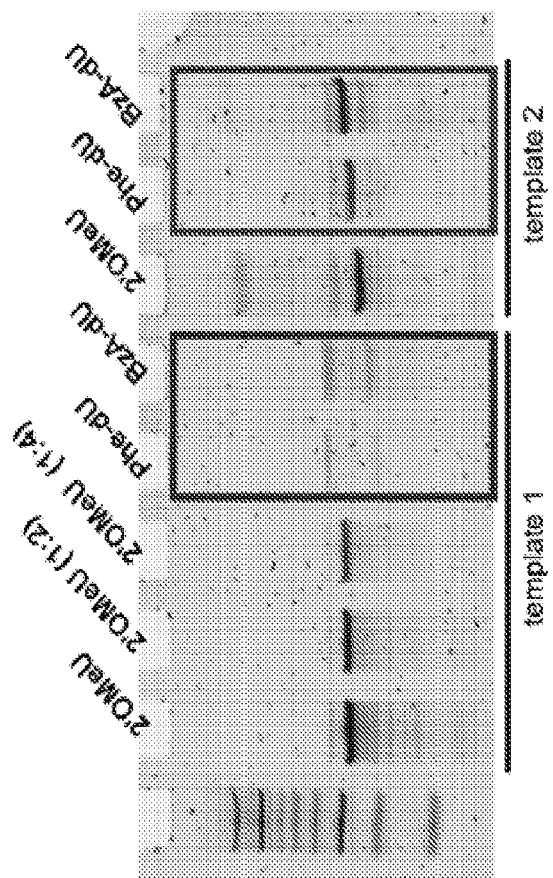
FIG. 2A-2B. Template sequence and addition of betaine effects transcription efficiency. A) The presence of T residues within the first 20 residues has a marked effect on the production of full length RNA library when transcribed using both PhedU and BzAdU, but not 2'OMeU. Template 1—SEQ ID NO:1; Template 2—SEQ ID NO:2. B) Positional effect of T residues on the efficiency of transcriptions using PhedU in the presence of and absence of 1M betaine. Right—Denaturing gel (7M urea) analysis of transcription reaction performed with and without 1M betaine. The identity of each template is indicated. Left—Quantitation of gel using densitometry. No betaine—6 left columns; betaine—6 right columns.
Figure 2B:
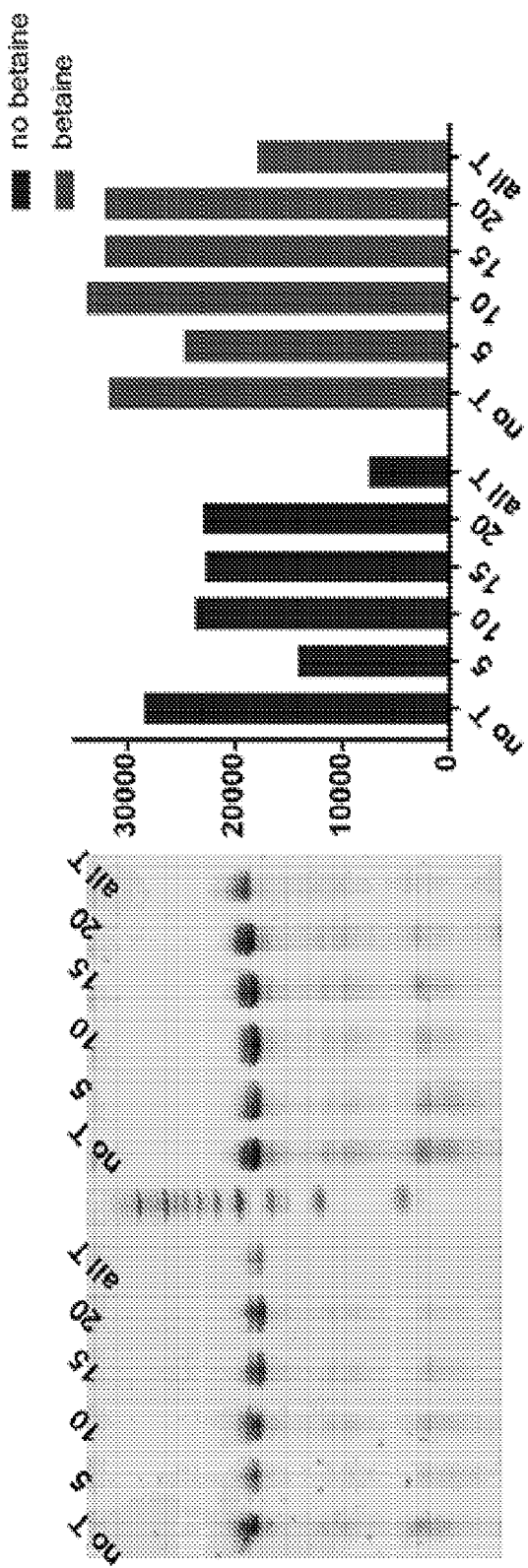

Preliminary experiments were used to identify optimal mutant T7 RNA polymerase enzyme, buffer conditions and more importantly, unique library characteristics, which were required to achieve efficient incorporation of this combination of modified nucleotide triphosphates. Most notably, while transcriptions using 2'OMe ATP, 2'OMe CTP, 2'F GTP and dTTP proceed efficiently, the incorporation of a modified dUTP residue (e.g., Phe-dUTP or BzA-dUTP; FIG. 1) was found to significantly inhibit the transcription reaction (FIG. 2A; template 1, left box). However, transcription efficiency can be rescued using templates that do not bear a T within the first 20 positions of the transcript (FIG. 2; template 2A, right box). Transcriptions yields were further improved by the addition of 2M betaine (FIG. 2B). With regard to polymerases, a T7 RNA polymerase variant bearing the following mutations Y639L, H784A and P266L (LAL-polymerase) was found to provide the best transcription yields with other variants proving less efficient (data not shown).

Having established conditions to generate modified RNAs composed of Phe-dUTP or BzA-dUTP in combination with 2'OMe ATP, 2'OMe CTP, 2'F GTP, it was next tested if this highly modified RNA could be converted back into DNA. To test this, a series of reverse transciptases were screened to assess the ability to extend a fluorescently labeled primer though a modified transcript. While MMLV and Thermoscript showed poor extension efficiency on these modified templates, the addition of the additive betaine, up to 2.5M, significantly improved these results using MMLV (data not shown). The MMLV variant, super script IV on the other hand proved even more capable a reading through the template, but also showed improved activity upon the addition of betaine (data not shown).

Having optimized the RT step, experiments were performed to ensure that following transcription and reverse transcription using these conditions, the identity of the template was not altered. That is, did the presence of the backbone modifications, or perhaps more importantly the modified deoxyuridine residues during transcription or reverse transcription result in miss-insertions, deletions or other alterations to the template sequence? To test this, a transcript was generated of a known RNA template using the mixture disclosed herein of Phe-dUTP, 2'OMe ATP, 2'OMe CTP and 2'F GTP and the LAL-polymerase or using a more traditional mixture, 2'F UTP, 2'F CTP, 2'OH ATP and 2'OH GTP and the Y639F-polymerase, which is commonly used to perform selection experiments (4). Following RT and PCR, 20 colonies were cloned and sequenced, and the sequences were compared to that of the known template. For transcripts generated using Phe-dUTP, 2'OMe ATP, 2'OMe CTP and 2'F GTP (PheMix), only 11 of the 22 (50%) sequences acquired were a perfect match with the starting template, whereas in the case of transcription performed using 2'F modified pyrimidines (2'FMix), 21 of 24 sequences were a perfect match (87.5%) (data not shown). Thus while the use of the PheMix appears to increase the appearance of mutations in the sequence, the error rate is not catastrophic. That is, for every two copies of the template made (1 cycle of PCR), on average one faithful copy of the template is generated. Indeed, at this rate, the introduction of such low levels of mutation may actually prove beneficial to the selection process, adding a low, but continual level of diversity to the selection process. However, many of the mutations for the PheMix appear to occur in the same position. For example, an A to T mutation at position 37 of the 78 nucleotide sequence is observed in 7 of 11 sequences suggesting that this may be mutation 'hot-spot' resulting perturbations in the oligonucleotide structure, sequence and the presence of the modified nucleotides (data not shown).

As an additional test to assess any biases, in particular a selection against sequences containing the Phe-dU residue, which might occur during transcription using the LAL-polymerase and PheMix, a naïve, Round 0, aptamer library was transcribed, and following transcription and reverse transcription using the present optimized methods, the nucleotide distribution observed for ~20 clones was compared with those generated from the same RNA library transcribed using 2'FMix and the Y639F-polymerase. As shown in Table 1, libraries generated using the PheMix demonstrated a roughly equal distribution of nucleotides to that observed from the library generated the 2'FMix. Most importantly the fraction of T residues in both libraries remains roughly equal suggesting that T containing sequences are not being selected against.

Example 1

Figure 3A:
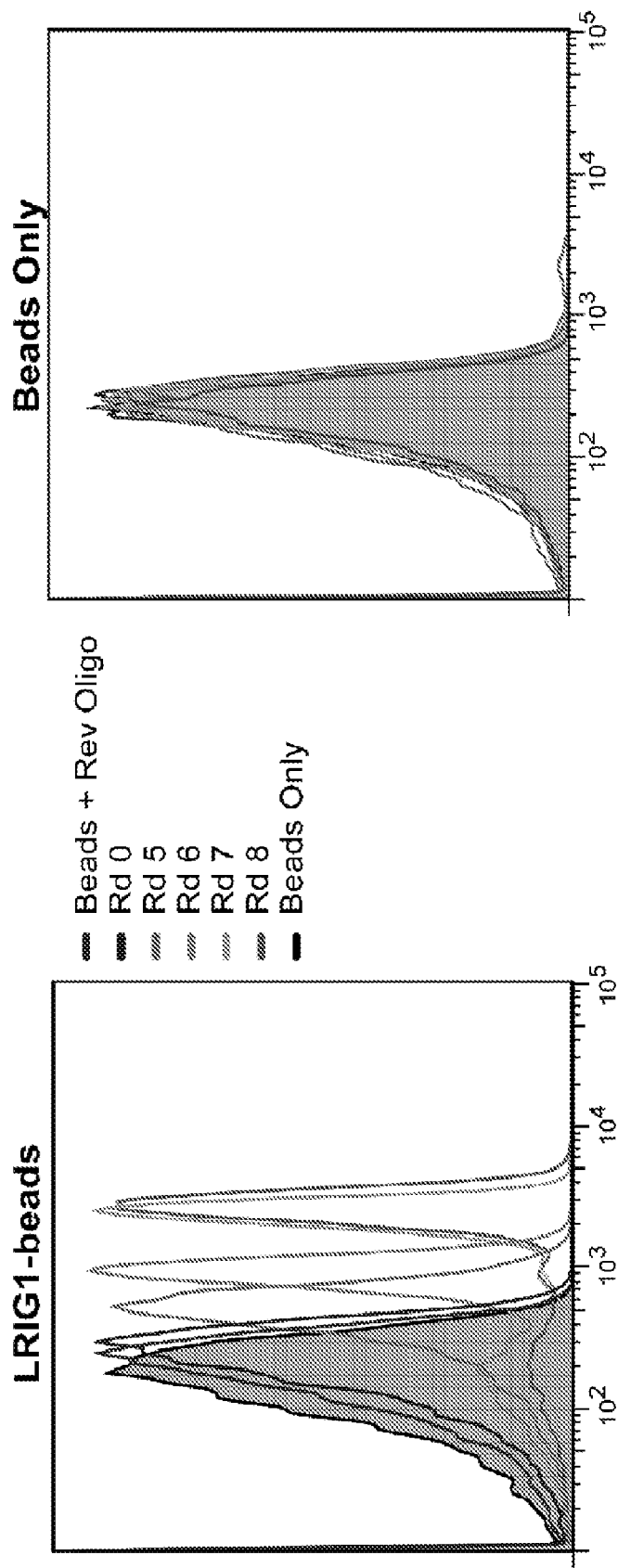
FIG. 3A-3B. Effect of selection rounds and use of hydrophobically modified residue on transcription efficiency. A) Progress of selection using library composed of 2'FG, 2'OMe A, 2'OMeC and Phe-dU. Selection progress was assessed by flow cytometry using fluorescently labeled libraries and beads bearing the target protein, LRIG-1-beads (left). The same experiment was performed using non-target bearing beads, Beads Only (right). B) Analysis of the Round 8 library (Rd8) transcribed using the modified dU derivative, Phe-dUTP or using dTTP (left). The structure of the dU derivative is shown without the triphosphate to aid in clarity (right).
Figure 3B:
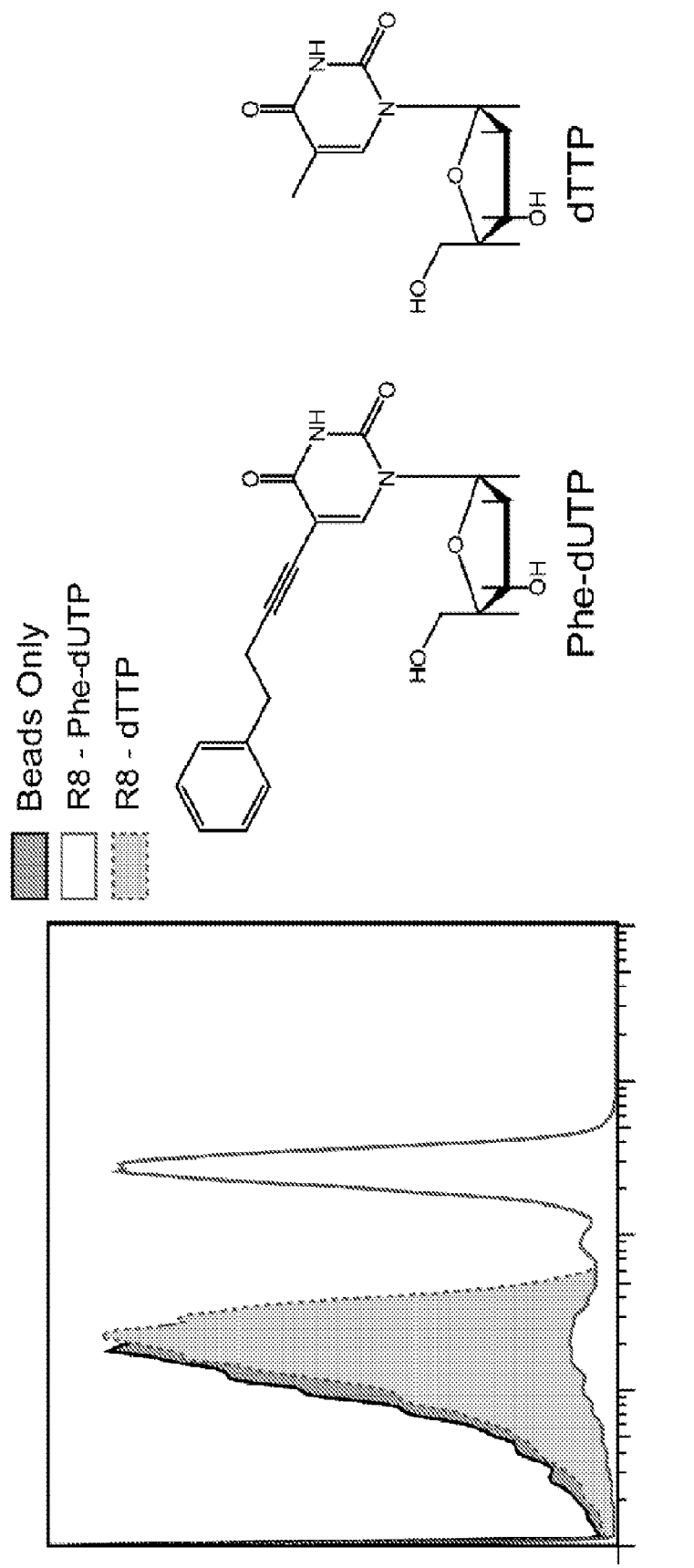
Figure 4:
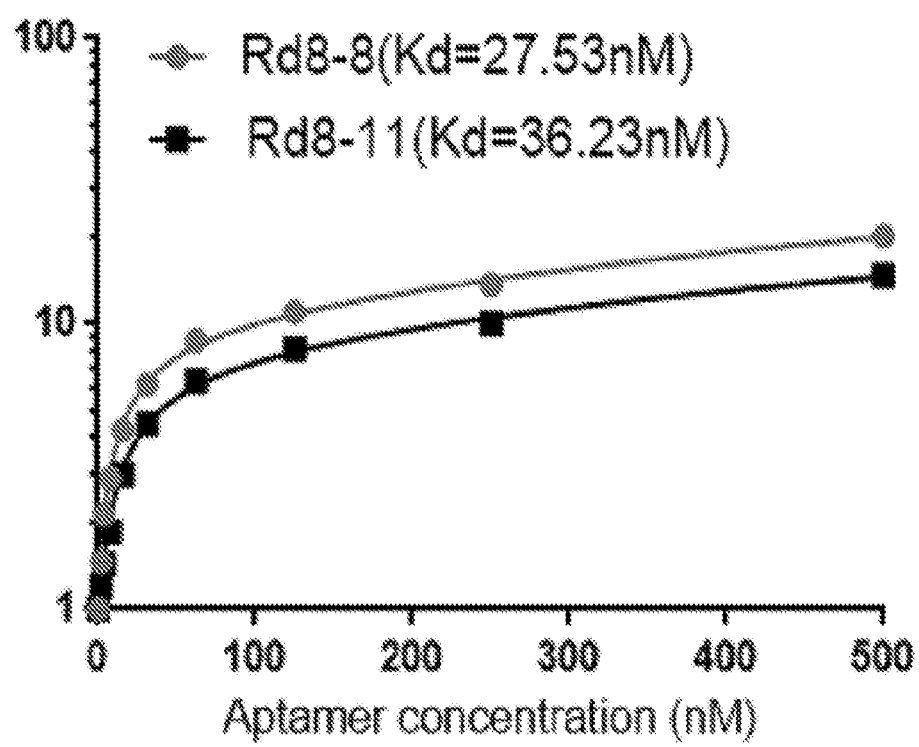
FIG. 4. Binding constant for two clones (clones 8 and 11) identified from the selection against LRIG-1 using a nucleotide library composed of 2'FG, 2'OMe A, 2'OMeC and Phe-dU. Binding constants were assessed by flow cytometry using Dynal His beads.

Using a N40 library containing ~10" unique sequences, transcribed using a mixture of Phe-dUTP, 2'OMe ATP, 2'OMe CTP and 2'F GTP, SELEX was initiated against the protein LRIG1. In short, the His-tagged protein was immobilized on 1 µm, magnetic His-capture beads and incubated with the library for 30 minutes at 37° C. after which the beads were washed 3 times with buffer, and then any bound library molecules eluted by the addition of wash buffer containing the denaturant guanidine hydrochloride (4M). Following elution the library molecules were recovered by ethanol precipitation and reverse transcribed into DNA using SSIV under optimized conditions (2M betaine). The resulting ssDNA was then amplified by PCR and the resulting dsDNA then transcribed back in to modified RNA by transcription using the LAL-polymerase and a mixture of Phe-dUTP, 2'OMe ATP, 2'OMe CTP and 2'F GTP under the present optimized conditions. The process was repeated for 8 rounds of selection. A fluorescently labeled library was used to monitor the selection by flow cytometry. Following the 5$^{th}$ round of selection, the library population demonstrated a detectable increase in binding to target loaded beads, which increased further in successive rounds (FIG. 3A). Importantly, when similar experiments were performed using non-protein target loaded beads, no signal over background was observed. Perhaps most importantly, when the Round 8 library was transcribed using a nucleotide mixture in which dTTP was substituted for the modified Phe-dUTP, the population lost all activity, indicating that the functional molecules in the population had an absolute requirement for this hydrophobically modified residue (FIG. 3B). Subsequent experiments were carried out to clone and sequence the round 6, 7 and 8 population and test individual molecules identified from the screen. Two clones identified from the selection, clones 8 and 11, display apparent binding constants of ~25 and 35 nM, respectively. Again, when the clones are incubated with non-protein loaded beads, no signal is observed (FIG. 4).

LRIG1 clones:
Lrig1-Rd8-08-full-seq (SEQ ID NO: 3)
GGGAAGGAGAGACGACGCGACACCCCCTTGAGTCACAGGTGTGTGAGCGC

CGACGGCTTGGTACAGCAGACAAGACCGGACAAGAAGC;

Lrig1-Rd8-11-full-seq (SEQ ID NO: 4)
GGGAAGGAGAGACGACGCGACACCCGCTTCACCGCTGTGTAACTGCGACG

ACGGACGTCAGATCAGCAGACAAGACCGGACAAGAAGC.

Example 2

Figure 5A:
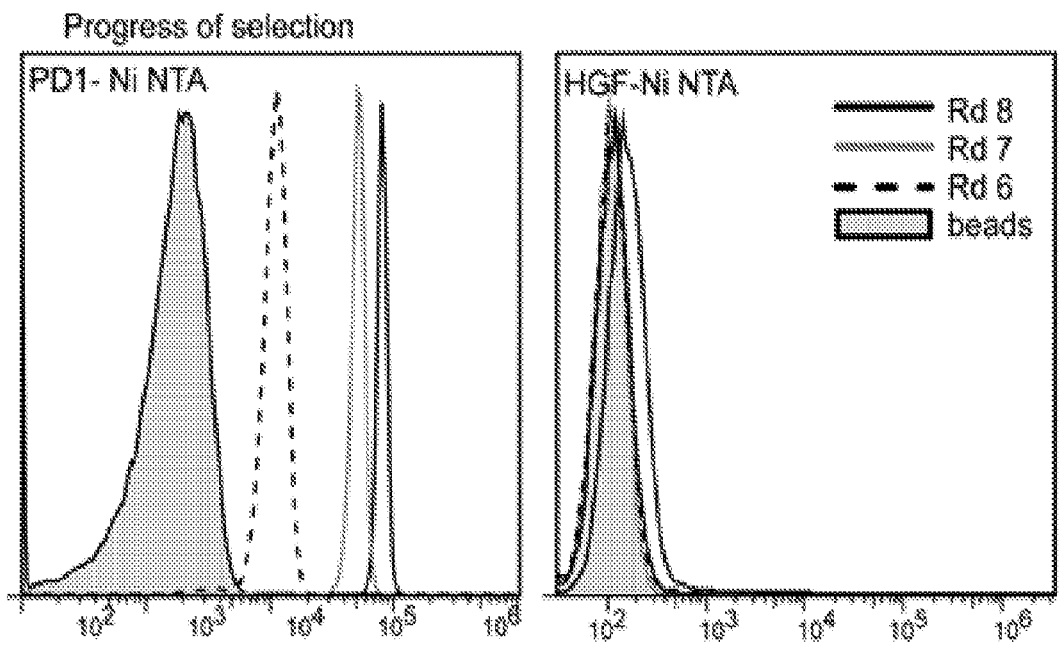
FIG. 5A-5B. Progress of selection against recombinant human PD-1 using a N40 RNA library composed of 2'FG, 2'OMe A, 2'OMeC and Phe-dU. A) Binding assays were performed using flow cytometry on recombinant hPD-1 bound beads using fluorescent RNA from rounds 6, 7 and 8 of the selection. Beads bearing human growth factor were used as a negative control. B) Analysis of the round 8 RNA population transcribed using 2'FG, 2'OMe A, 2'OMeC and Phe-dU (Rd8 PhedU) or 2'FG, 2'OMe A, 2'OMeC and T (Rnd 8 T).
Figure 5B:
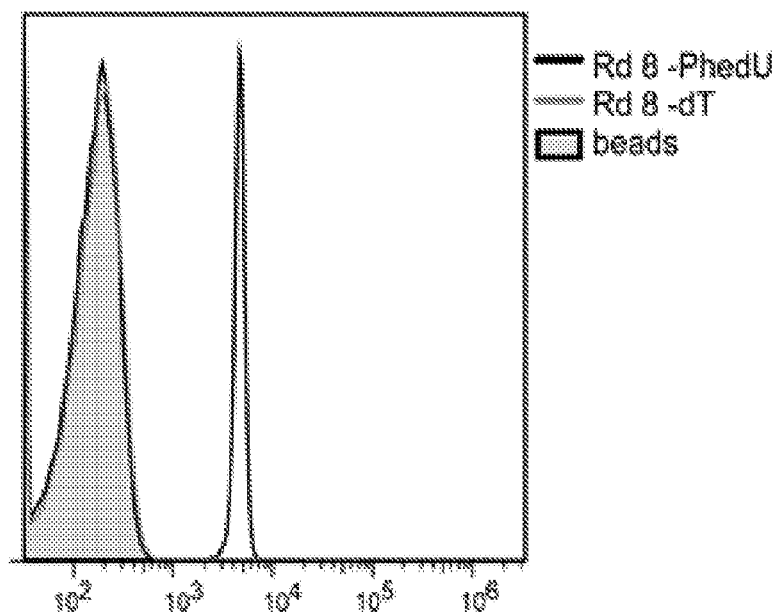
Figure 6A:
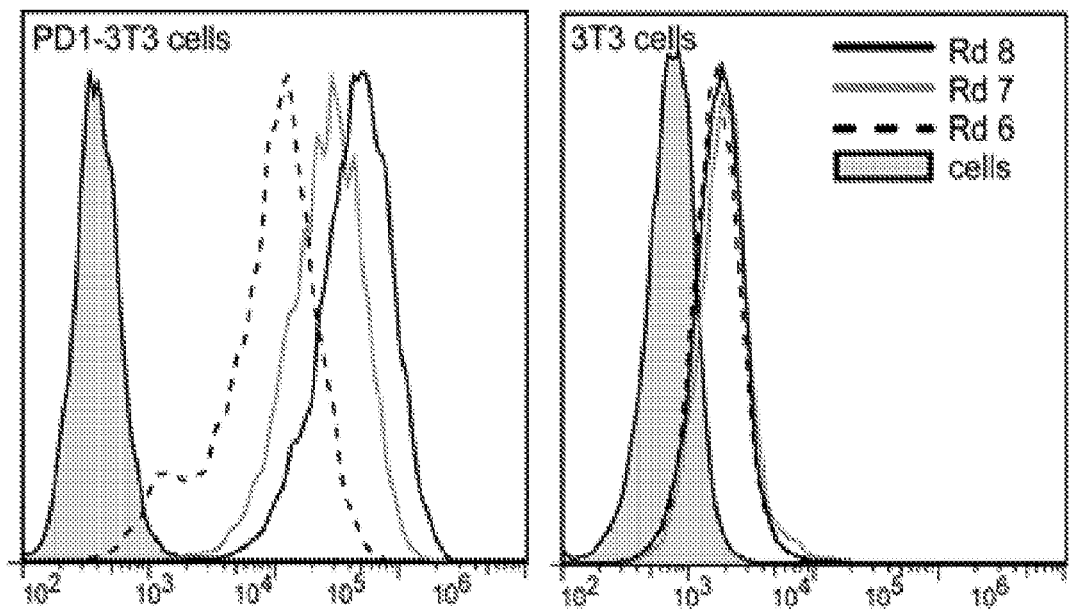
FIG. 6A-6B. Progress of selection against human PD-1 using a N40 RNA library composed of 2'FG, 2'OMe A, 2'OMeC and Phe-dU. A) Binding assays were performed using flow cytometry on mouse 3T3 cells engineered to express human PD1 (PD1-3T3) using fluorescent RNA from rounds 6, 7 and 8 of the selection. The parental 3T3 cells served as a negative control. B) Analysis of the round 8 RNA population transcribed using 2'FG, 2'OMe A, 2'OMeC and Phe-dU (Rd8 PhedU) or 2'FG, 2'OMe A, 2'OMeC and T (Rnd 8 T) on PD1-3T3 cells.
Figure 6B:
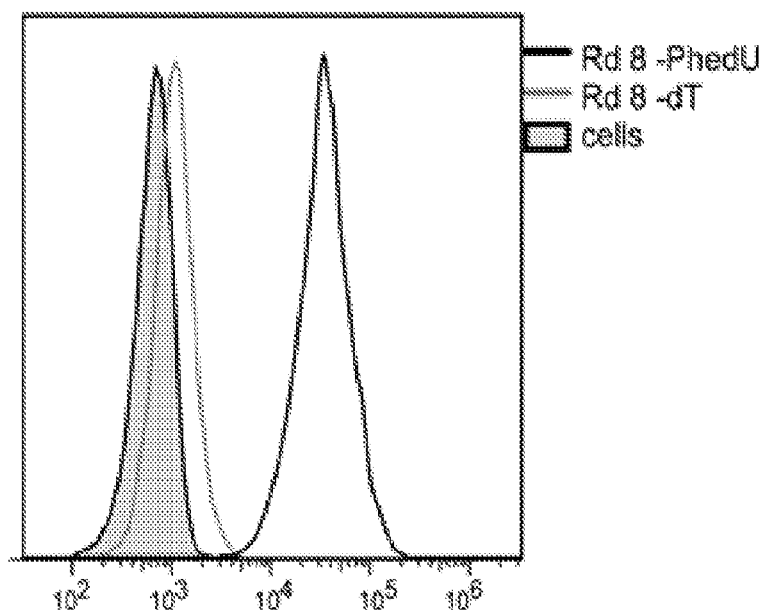

Using a N40 library containing ~1014 unique sequences, transcribed using a mixture of Phe-dUTP, 2'OMe ATP, 2'OMe CTP and 2'F GTP, SELEX was initiated against Programmed cell death protein 1 (PD1). The initial 5 rounds of the selection were carried out in the same way as described above. For rounds 6 and 7, the negative selection step was carried out on NIH-3t3 cells which do not express PD1, followed by a positive selection on the target protein immobilized on Ni-NTA beads. In round 8, the positive selection was carried out on engineered NIH-3T3 cells overexpressing PD1, following a negative selection on wild type NIH-3T3 cells which do not express PD1. This was done to ensure the enrichment of aptamers which binds to PD1 on cell surface. For rounds 6, 7 and 8, in the positive selection stage, 0.1 mM Dextran Sulphate (18 kd) was also added to the PD1-Ni-NTA beads/PD1 expressing cells to enhance the stringency. For the cell selection step in round 8, following negative selection, the pool was incubated with 100,000 PD1 expressing cells at 37° C. for 1 hour in DMEM media with ssDNA and 0.1 mM Dextran Sulphate. After this, the cells were washed with HBSS and the RNA was trizol extracted. The reverse transcription and subsequent PCR and transcription were carried out as described above. As shown in FIG. 5A, Rounds 6, 7 and 8 show demonstrate significant, PD1 dependent staining Ni-NTA beads as assessed by flow cytometry. Importantly when round 8 was transcribed using dT in place of the modified nucleotide PhedU, the library lost all activity (FIG. 5B). Similar staining is observed on hPD1-3T3 cells, a cell line engineered to express human PD1 (FIG. 6A), but not the parental 3T3 cell line, confirming specificity. Again, transcription of the round 8 population with dT in place of PhedU resulted in a loss of staining activity on PD1 positive cells (FIG. 6B).

Figure 7A:
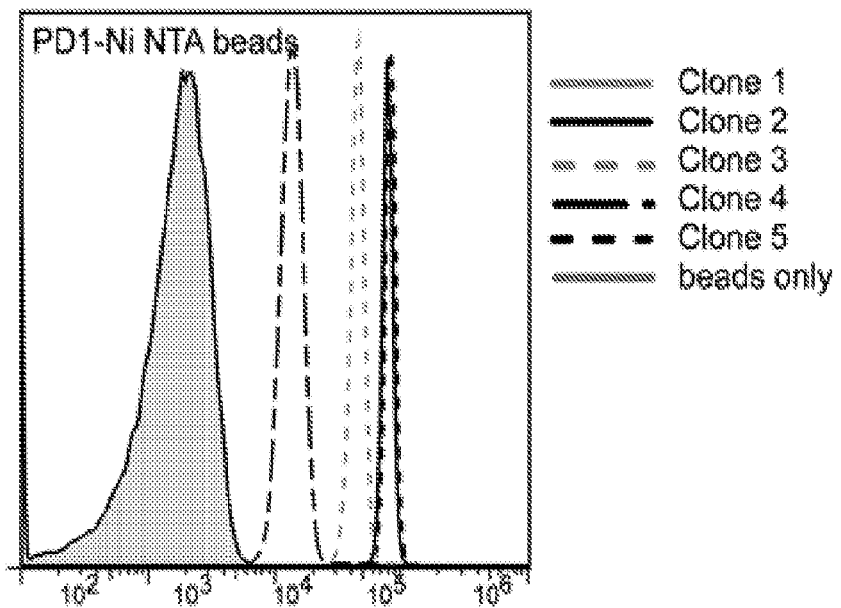
FIG. 7A-7D. Analysis of clones from selection targeting human PD-1 using a N40 RNA library composed of 2'FG, 2'OMe A, 2'OMeC and Phe-dU. A) Binding to hPD-1 bound beads using 100 nM aptamer. B) Binding to PD1-3T3 cells using 100 nM aptamers. C) and D) Functional analysis of Clone 2 transcribed using T in place of PhedU on immobilized recombinant protein C) and PD-1-3T3 cells.
Figure 7B:
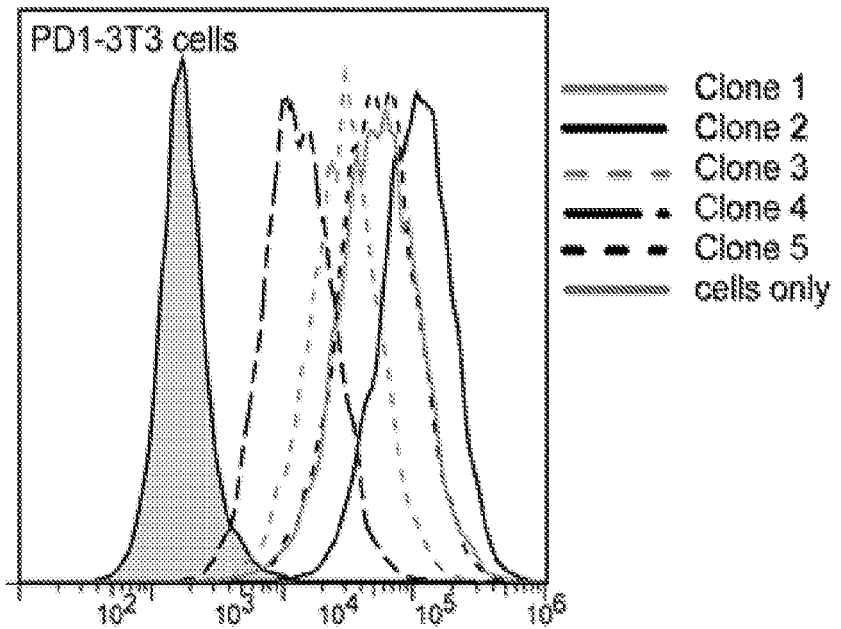
Figure 7C:
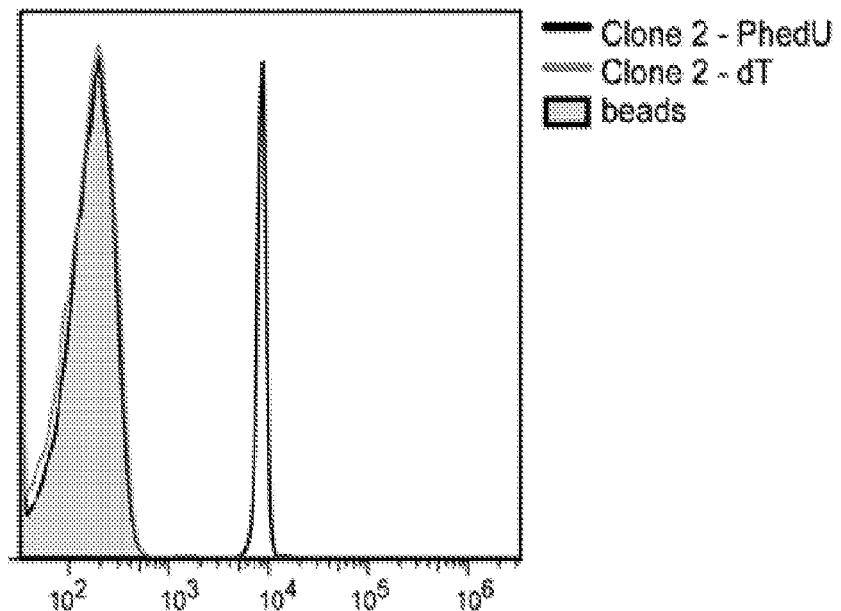
Figure 7D:
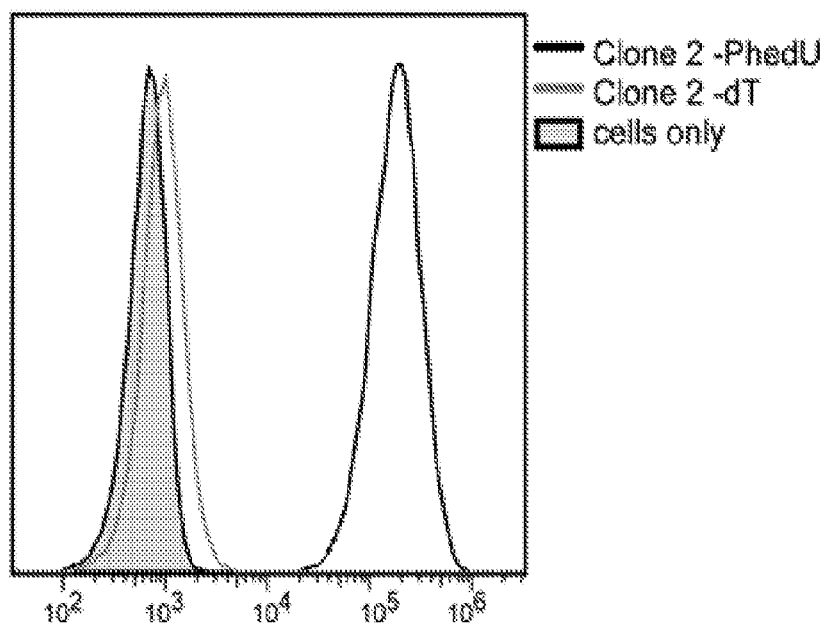

Sequence analysis of the Round 8 library lead to the identification of clones capable of specifically binding PD1. As shown in FIG. 7, individual clones demonstrated binding to both recombinant protein (FIG. 7A) as well as hPD1-expressing 3T3 cells (FIG. 7B). As observed with individual rounds, when individual clones were transcribed, as exemplified by Clone 2 with dT rather than Phe-dU, binding to recombinant protein (FIG. 7C) or hPD1-expressing 3T3 cells (FIG. 7D) was lost, demonstrating the dependence on this unique modification for function.

Figure 8:
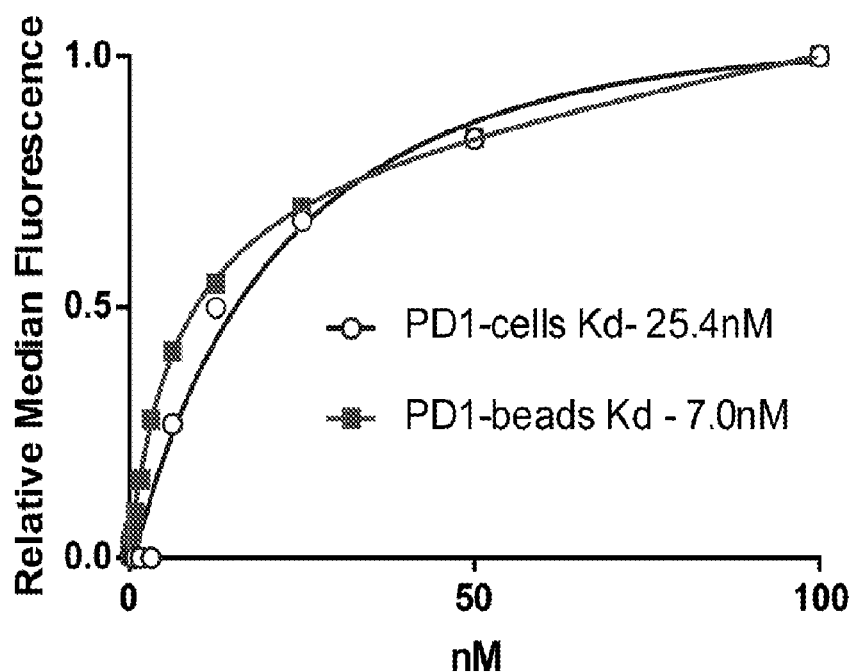
FIG. 8. Determination the binding constant for anti-PD1 clone 2. Binding constants were determined by incubated at increasing concentrations with hPD-1 bound beads or hPD1-3T3 cells.
Figure 9:
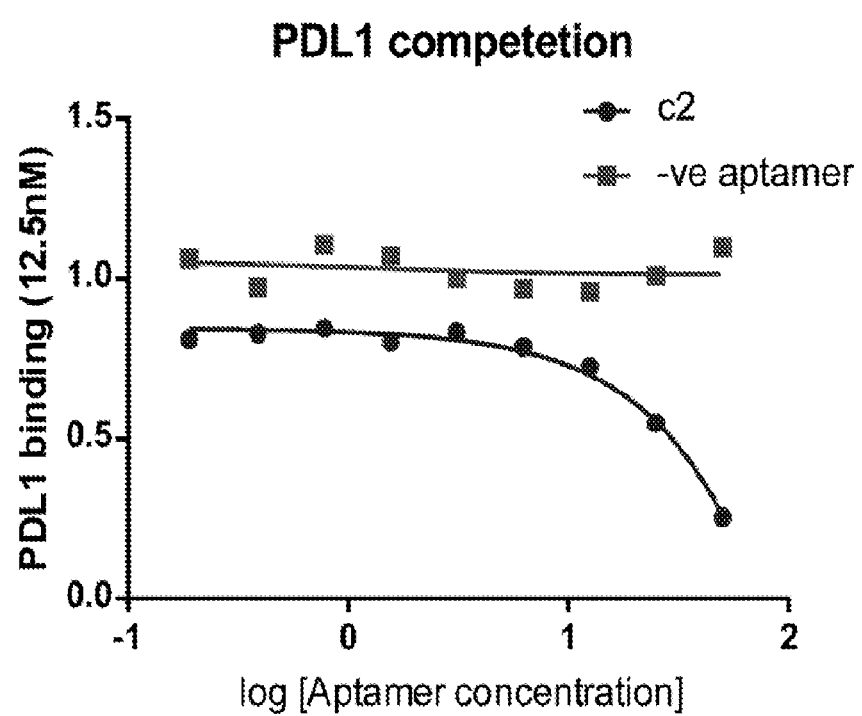
FIG. 9. Clone 2 (c2) competes with PDL1-Fc for binding with PD1. PD1-3T3 cells were incubated with 12.5 nM PD1 and increasing concentrations of clone 2. Following incubation, cells were washed and bound PDL1 was detected using an anti-Fc antibody followed by flow cytometry. IC50=~35 nM.

The best performing molecule, clone 2 demonstrated a binding constant of ~7 nM on recombinant human PD1 and apparent binding constant of ~25 nM on hPD1-expressing 3T3 cells (FIG. 8) and competes with PDL1, a natural ligand for this receptor with a IC50 of ~30 nM (FIG. 9).

PD1 clone 2 truncations:

(SEQ ID NO: 5)
GGGAAGGAGAGACGACGCGACACTCGAAAATGCTGGAGTAACTTCTTAGA

GTACTTGGC;

(SEQ ID NO: 6)
GGGAGAGACGACGCGACACTCGAAAATGCTGGAGTAACTTCTTAGAGTAC

TTGGC;

(SEQ ID NO: 7)
GGGCGACGCGACACTCGAAAATGCTGGAGTAACTTCTTAGAGTACTTGGC;

(SEQ ID NO: 8)
CGACGCGACACTCGAAAATGCTGGAGTAACTTCTTAGAGTACTTGGC.

TABLE 1

Distribution of nucleotides observed in 20 sequences from the Round 0 library transcribed using Phe-dUTP, 2'OMe ATP, 2'OMe CTP and 2'F GTP (PheMix) and the LAL-polymerase or a more traditional mixture, 2'F UTP, 2'F CTP, 2'OH ATP and 2'OH GTP (2'FMix) and the Y639F-polymerase.

|   | 2'FMix | PheMix |
|---|--------|--------|
| A | 28.5%  | 26.8%  |
| C | 25.8%  | 27.1%  |
| G | 19.8%  | 23.9%  |
| T | 26.0%  | 22.2%  |

REFERENCES

1. Maier, K. E. and Levy, M. (2016) From selection hits to clinical leads: progress in aptamer discovery. *Mol Ther Methods Clin Dev,* 5, 16014.
2. Rohloff, J. C., Gelinas, A. D., Jarvis, T. C., Ochsner, U. A., Schneider, D. J., Gold, L. and Janjic, N. (2014) Nucleic Acid Ligands With Protein-like Side Chains: Modified Aptamers and Their Use as Diagnostic and Therapeutic Agents. *Mol Ther Nucleic Acids,* 3, e201.
3. Gold, L., Ayers, D., Bertino, J., Bock, C., Bock, A., Brody, E. N., Carter, J., Dalby, A. B., Eaton, B. E., Fitzwater, T. et al. (2010) Aptamer-based multiplexed proteomic technology for biomarker discovery. *PLoS One,* 5, e15004.
4. Padilla, R. and Sousa, R. (1995) Mutant T7 Rna-Polymerase as a DNA-Polymerase. *Embo Journal,* 14, 4609-4621.
5. Famulok, M. (1999) Oligonucleotide aptamers that recognize small molecules. *Curr Opin Struct Biol,* 9, 324-329.
6. Xu, W. and Ellington, A. D. (1996) Anti-peptide aptamers recognize amino acid sequence and bind a protein epitope. *Proc Natl Acad Sci USA,* 93, 7475-7480.
7. Tuerk, C. and Gold, L. (1990) Systematic evolution of ligands by exponential enrichment: RNA ligands to bacteriophage T4 DNA polymerase. 249, 505-510.
8. Daniels, D. A., Chen, H., Hicke, B. J., Swiderek, K. M. and Gold, L. (2003) A tenascin-C aptamer identified by tumor cell SELEX: systematic evolution of ligands by exponential enrichment. *Proc Natl Acad Sci USA,* 100, 15416-15421.
9. Shangguan, D., Li, Y., Tang, Z., Cao, Z. C., Chen, H. W., Mallikaratchy, P., Sefah, K., Yang, C. J. and Tan, W. (2006) Aptamers evolved from live cells as effective molecular probes for cancer study. *Proc Natl Acad Sci USA,* 103, 11838-11843.
10. Magalhaes, M. L., Byrom, M., Yan, A., Kelly, L., Li, N., Furtado, R., Palliser, D., Ellington, A. D. and Levy, M. (2012) A general RNA motif for cellular transfection. *Mol Ther,* 20, 616-624.
11. Jenison, R. D., Gill, S. C., Pardi, A. and Polisky, B. (1994) High-resolution molecular discrimination by RNA. Science, 263, 1425-1429.
12. Ni, X., Castanares, M., Mukherjee, A. and Lupold, S. E. (2011) Nucleic acid aptamers: clinical applications and promising new horizons. *Curr Med Chem,* 18, 4206-4214.

What is claimed is:

1. A method for preparing a chemically modified ribonucleic acid (RNA) aptamer that binds to a target in a tissue or cell sample or surface or to a target protein or small molecule, the method comprising:
contacting a candidate mixture of RNAs with the tissue or cell sample, surface, protein or small molecule, wherein the mixture comprises 2'F guanylate, 2'OMe cytidylate, 2'OMe adenylate, and a deoxy pyrimidine nucleotide with a moiety on the 5 position of the pyrimidine, wherein the mixture of RNAs are transcribed from a DNA template having no thymine residues within a first 20 nucleotides of its transcript, and wherein RNAs having affinity to the target bind the target and form RNA-target complexes;

separating RNA-target complexes from free RNAs in the candidate mixture; and identifying chemically modified RNAs that bind to the target in the tissue or cell sample, surface, protein or small molecule, thereby preparing a chemically modified RNA aptamer that binds to a target in a tissue or cell sample or surface or to a target protein or small molecule.

2. The method of claim 1, wherein the aptamer is prepared using iterative rounds of selection against the target.

3. The method of claim 1, wherein the candidate mixture of RNAs is contacted with the tissue or cell sample, surface, protein or small molecule, and with a T7 RNA polymerase having one or more of the following mutations: Y639L, H784A and P266L.

4. The method of claim 3, wherein the T7 RNA polymerase is a LAL-polymerase comprising the following mutations: Y639L, H784A and P266L.

5. The method of claim 1, wherein the mixture comprises a buffer comprising 40 mM Tris [pH 8.3], 40 mM dithiothreitol, 1 mM spermidine, 0.01% Triton X-100, 50 mg/ml PEG-8000, 25 mM $MgCl_2$ and 10 mM $MnCl_2$.

6. The method of claim 1, wherein the mixture comprises betaine.

7. The method of claim 6, wherein betaine is present at a final concentration of at least 1 M.

8. The method of claim 6, wherein betaine is present at a final concentration of 1-2.5 M.

9. The method of claim 1, wherein the deoxy pyrimidine nucleotide with a moiety of the 5 position of the pyrimidine is a modified deoxyuridine, 2'OMe, 2'$NH_2$, 2'H or locked nucleic acid residue.

10. The method of claim 1, wherein the deoxy pyrimidine nucleotide with a moiety on the 5 position of the pyrimidine is Phe-dUTP, Bza-dUTP, isobutyl-dUTP, tyrosyl-dUTP, napthyl-dUTP, Phe-dCTP, Bza-dCTP, isobutyl-dCTP, tyrosyl-dCTP, or napthyl-dCTP.

11. The method of claim 1, wherein the deoxy pyrimidine nucleotide with a moiety on the 5 position of the pyrimidine consists of a triphosphate of a structure selected from the following:

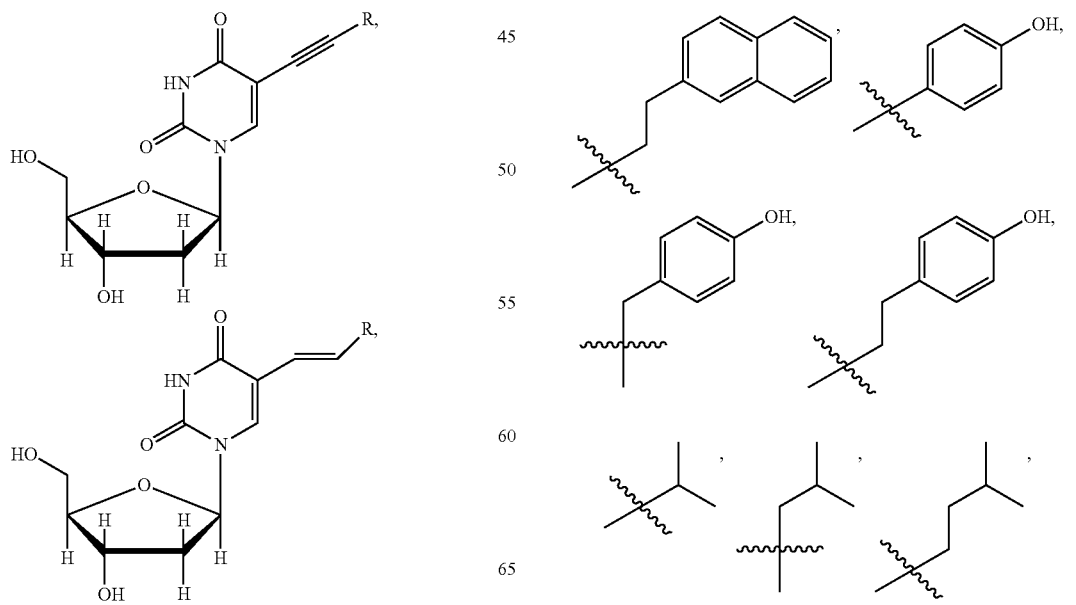

wherein R is

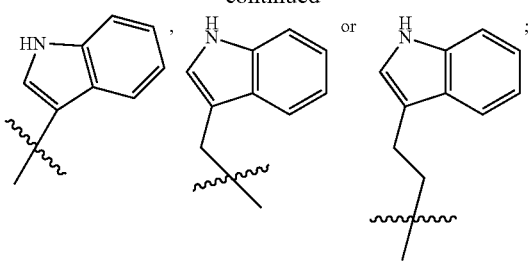

wherein z# represents the point of attachment of the R group to the pyrimidine or modified pyrimidine.

12. The method of claim 9, wherein Phe-dUTP, Bza-dUTP, isobutyl-dUTP, tyrosyl-dUTP, Phe-dCTP, Bza-dCTP, Bza-dCTP, isobutyl-dCTP, tyrosyl-dCTP, or napthyl-dCTP or the 5'-modified deoxy pyrimidine nucleotide is present in a concentration of 1-2.5 mM.

13. The method of claim 9, wherein Phe-dUTP, Bza-dUTP, isobutyl-dUTP, tyrosyl-dUTP, napthyl-dUTP, Phe-dCTP, Bza-dCTP, isobutyl-dCTP, tyrosyl-dCTP, or napthyl-dCTP or the 5'-modified deoxy pyrimidine nucleotide is present in a concentration of 2 mM.

14. The method of claim 1, wherein the moiety on the 5 position of the pyrimidine is a hydrophobic moiety.

15. The method of claim 1, wherein one or more of 2'F guanylate, 2'OMe cytidylate and 2'OMe adenylate is present in a concentration of 25 mM.

16. The method of claim 1, wherein the aptamer comprises one or more of nucleotide sequence (SEQ ID NO: 3)
GGGAAGGAGAGACGACGCGACACCCCCTTGAGTCACAGGTGTGTGAGCGC

CGACGGCTTGGTACAGCAGACAAGACCGGACAAGAAGC and (SEQ ID NO: 4)
GGGAAGGAGAGACGACGCGACACCCGCTTCACCGCTGTGTAACTGCGACG

ACGGACGTCAGATCAGCAGACAAGACCGGACAAGAAGC.

17. The method of claim 1, wherein the aptamer comprises one or more of nucleotide sequence (SEQ ID NO: 5)
GGGAAGGAGAGACGACGCGACACTCGAAAATGCTGGAGTAACTTCTTAGA

GTACTTGGC;

(SEQ ID NO: 6)
GGGAGAGACGACGCGACACTCGAAAATGCTGGAGTAACTTCTTAGAGTAC

TTGGC;

(SEQ ID NO: 7)
GGGCGACGCGACACTCGAAAATGCTGGAGTAACTTCTTAGAGTACTTGGC;

and (SEQ ID NO: 8)
CGACGCGACACTCGAAAATGCTGGAGTAACTTCTTAGAGTACTTGGC.

18. A chemically modified ribonucleic acid (RNA) aptamer comprising one or more of 2'F guanylate, 2'OMe cytidylate, 2'OMe adenylate, and a modified deoxy pyrimidine nucleotide with a moiety on the 5 position of the pyrimidine, wherein the RNA aptamer has no uridine residues within the first 20 nucleotides.

* * * * *